(12) United States Patent
Garel et al.

(10) Patent No.: US 9,284,247 B2
(45) Date of Patent: Mar. 15, 2016

(54) METHOD FOR PRODUCING ALKOXY-HYDROXYBENZALDEHYDE THAT IS SUBSTANTIALLY FREE OF ALKYL-ALKOXY-HYDROXYBENZALDEHYDE

(71) Applicant: RHODIA OPERATIONS, Paris (FR)

(72) Inventors: Laurent Garel, Lyon (FR); Hubert Gayet, Saint Priest (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/417,010

(22) PCT Filed: Jul. 12, 2013

(86) PCT No.: PCT/EP2013/064859
§ 371 (c)(1),
(2) Date: Jan. 23, 2015

(87) PCT Pub. No.: WO2014/016145
PCT Pub. Date: Jan. 30, 2014

(65) Prior Publication Data
US 2015/0203428 A1    Jul. 23, 2015

(30) Foreign Application Priority Data

Jul. 26, 2012 (FR) ..................... 1257280

(51) Int. Cl.
| | | |
|---|---|---|
| C07C 45/32 | (2006.01) | |
| C07C 45/38 | (2006.01) | |
| C07C 41/09 | (2006.01) | |
| C07C 41/42 | (2006.01) | |
| C07C 45/39 | (2006.01) | |
| C07C 51/367 | (2006.01) | |
| C07C 51/353 | (2006.01) | |

(52) U.S. Cl.
CPC .......... *C07C 45/38* (2013.01); *C07C 41/09* (2013.01); *C07C 41/42* (2013.01); *C07C 45/39* (2013.01); *C07C 51/353* (2013.01); *C07C 51/367* (2013.01)

(58) Field of Classification Search
CPC ...... C07C 45/32; C07C 45/455; C07C 37/055
USPC ....................................... 568/432
See application file for complete search history.

(56) References Cited

U.S. PATENT DOCUMENTS

| | | | |
|---|---|---|---|
| 4,165,341 A | | 8/1979 | Umemura et al. |
| 5,105,029 A | * | 4/1992 | Ninomiya et al. ............ 568/872 |
| 5,430,183 A | | 7/1995 | Nobel |
| 6,753,441 B1 | | 6/2004 | Jouve et al. |
| 2011/0009664 A1 | | 1/2011 | Heinisch et al. |
| 2011/0230674 A1 | | 9/2011 | Desouhant-Massacret |
| 2011/0306802 A1 | | 12/2011 | Maliverney et al. |
| 2012/0103786 A1 | | 5/2012 | Gayet et al. |
| 2012/0264982 A1 | | 10/2012 | Desouhant-Massacret |

FOREIGN PATENT DOCUMENTS

| | | |
|---|---|---|
| CN | 101492353 A | 7/2009 |
| CN | 102010310 A | 4/2011 |
| EP | 0509927 A1 | 10/1992 |
| EP | 0578550 A1 | 1/1994 |
| EP | 0873786 A1 | 10/1996 |
| EP | 0914854 A2 | 5/1999 |
| EP | 0933107 A1 | 8/1999 |
| FR | 2664266 A1 | 1/1992 |
| FR | 2379501 A1 | 12/2011 |
| WO | WO 9965853 A1 | 12/1999 |
| WO | WO 2008148760 A1 | 12/2008 |
| WO | WO 2009077383 A1 | 6/2009 |
| WO | WO 2009141280 A1 | 11/2009 |
| WO | WO 2010007161 A1 | 1/2010 |
| WO | WO 2011039331 A1 | 4/2011 |
| WO | WO 2014/016146 A1 | 1/2014 |

OTHER PUBLICATIONS

Bjorsvik et al. High Selectivity in the Oxidation of Mandelic Acid Derivatives and in O-Methylation of Protocatechualdehyde: New Process fof Synthesis of Vanillin, iso-Vanillin, and Heliotropin. Organic Process Research & Development, 2000, vol. 4, 534-543.*
Bjorsvik et al.—High Selectivity in the Oxidation of Mandelic Acid Derivatives and in O-Methylation of Photocatechualdehyde: New Processes for Synthesis of Vanillin, iso-Vanillin, and Heliotropin, Organic Process Research & Development (2000), vol. 4, No. 6, 534-543 (10 pages).
U.S. Appl. No. 14/417,015, filed Jan. 23, 2015, Garel.
Office Action issued in Chinese Patent Application No. 201380012015.3; Dated Jun. 23, 2015 (7 pages).

* cited by examiner

*Primary Examiner* — Sikarl Witherspoon
(74) *Attorney, Agent, or Firm* — Osha Liang LLP (57) ABSTRACT

The invention relates to a method for producing at least one alkoxy-hydroxybenzaldehyde (AHBA) from at least one hydroxyphenol (HP), said method being characterized in that it comprises the formation of at least one alkoxyphenol (AP) and alkyl-alkoxyphenol (AAP) and the separation (S) of AP from AAP, said separation (S) being carried out prior to obtaining AHBA.

17 Claims, 3 Drawing Sheets

METHOD FOR PRODUCING ALKOXY-HYDROXYBENZALDEHYDE THAT IS SUBSTANTIALLY FREE OF ALKYL-ALKOXY-HYDROXYBENZALDEHYDE

This application is a U.S. national stage entry under 35 U.S.C. §371 of International Application No. PCT/EP2013/064859, filed Jul. 12, 2013, which claims priority to French Application No. 1257280 filed on Jul. 26, 2012. The entire content of each of these applications is hereby incorporated herein.

The present invention relates to the production of alkoxy-hydroxybenzaldehyde ("AHBA") and in particular to the production thereof as purely as possible.

The invention relates more particularly to the production of AHBA from hydroxyphenol ("HP").

The invention relates even more specifically to the production of vanillin ("VA") and/or of ethylvanillin ("EVA").

PRIOR ART

Alkoxyhydroxybenzaldehydes ("AHBAs") are very important products used first as flavorings and fragrances and then subsequently as intermediate products in numerous fields, for instance agrochemistry, the pharmaceutical industry, the cosmetics industry and other industries.

In particular, vanillin and ethylvanillin are products that are essentially intended for foods. It is therefore important to offer on the market products which are of high chemical purity and of good taste quality while at the same time ensuring a marketing cost that is as low as possible.

Thus, the process for synthesizing said products requires an improvement in the chemical reactions carried out and the performing of efficient separation and purification operations.

Various processes have been proposed for the synthesis of aromatic aldehydes. The most significant processes are based on the functionalization of a starting phenolic compound, for example phenol, catechol (also called pyrocatechol or "PC"), a catechol derivative, guaiacol (or 2-methoxyphenol) and/or guaethol (or 2-ethoxyphenol). In this type of process, the phenolic compound is generally used in a salified form, for example, in the form of a sodium salt: a formyl group is added in the para position with respect to the hydroxyl group present on the benzene ring, according to various methods.

To produce guaiacol, some processes consist in choosing ortho-nitrochlorobenzene (ONCB) as starting material.

These processes have many drawbacks compared with the process starting from pyrocatechol: handling of CMR (carcinogenic, mutagenic and toxic to reproduction) toxic compounds, such as o-anisidine; numerous steps; exothermic and dangerous reactions, such as nitration or hydrolysis of a diazonium salt; generation of numerous effluents; formation of impurities, such as 5-chloroguaiacol, which is in vanillin in the form of 6-chlorovanillin, etc.

Moreover, there is a completely different route for obtaining vanillin, which consists in reacting guaiacol and glyoxylic acid in a basic medium, resulting in 4-hydroxy-3-methoxy-mandelic acid, and then in oxidizing the condensate obtained.

Synthesizing guaiacol (GA) or guaethol (GE) from catechol is much more direct.

Processes for synthesizing para-methoxyphenol (PMP) and/or para-ethoxyphenol (PEP) from hydroquinone also exist.

Compounds such as GA, GE, PMP and PEP are alkoxyphenols ("APs").

The addition of an aldehyde function to an alkoxyphenol ("AP") so as to give AHBA can be carried out by means of a reaction between AP and glyoxylic acid, then oxidation of the resulting compound. However, AHBA prepared according to this route comprises in particular the alkylalkoxyhydroxy-benzaldehyde ("AAHBA") compound as impurity. As it happens, this mixture is particularly difficult to separate.

Because of this difficult separation, the AHBA/AAHBA mixture is separated by crystallization, which involves the use of organic solvents.

This problem arises more especially during the production of vanillin ("VA") or ethylvanillin ("EVA") from benzene-1, 2-diol (catechol, or pyrocatechol, termed "PC" in the present invention) because the methylated impurity of vanillin or the ethylated impurity of ethylvanillin is very difficult to separate from VA and/or EVA.

Generally, the use of organic solvents is relatively undesired owing in particular to the toxicity of the organic solvents that can be used, to the additional costs generated by their use, or to the treatment of the solvent for recycling or regeneration purposes.

AIMS OF THE INVENTION

Thus, an aim of the present invention is to solve the above-mentioned problems.

In particular, the main aim of the present invention is to improve the existing industrial processes for producing alkoxyhydroxybenzaldehydes ("AHBAs"), and in particular vanillin ("VA") and/or ethylvanillin ("EVA"), especially from the point of view of the purity of the AHBA, and in particular of vanillin (VA) and/or of ethylvanillin (EVA).

An aim of the invention is in particular to obtain these compounds substantially free of alkylalkoxyhydroxybenzaldehyde ("AAHBA") impurities, and in particular of 5-methyl-vanillin ("MEVA") and of 5-ethyl-ethylvanillin ("EEVA"), during the production of at least one alkoxyhydroxybenzaldehyde compound, and typically of vanillin and/or of ethylvanillin.

An aim of the invention is also to optimize such industrial processes, and in particular to improve the AHBA yields of the existing processes with a maximum AHBA purity.

A particular aim of the invention is to provide a process for purifying a stream of VA and/or EVA, in which VA and/or EVA is prepared from GA and/or GE.

A particular aim of the invention is also to provide a process for purifying a stream of VA and/or EVA, in which VA and/or EVA is prepared from PC.

An aim of the invention is in particular to provide such processes when they comprise a vapor-phase reaction for O-alkylation of hydroxyphenol so as to form the corresponding alkoxyphenol.

An aim of the present invention is to manufacture the alkoxyphenol compound industrially with a good yield, a low production of impurities and/or efficient removal thereof, and a high hydroxyphenol conversion. However, for example for a process which makes it possible to produce guaiacol, the formation of veratrole also occurs, obtained via an additional (successive) methylation of guaiacol.

Thus, an aim of the present invention is to limit the presence of the dialkoxybenzene impurity generated during the production of at least one alkoxyphenol from at least one hydroxyphenol. An aim of the present invention is in particular to limit the presence of veratrole during the synthesis of guaiacol.

SUMMARY OF THE INVENTION

The present invention makes it possible to solve the above-mentioned problems.

The present invention makes it possible to produce an alkoxyhydroxybenzaldehyde compound industrially with a high purity while at the same time preserving a synthesis with good yields, a low production of impurities and/or efficient removal thereof, and a high conversion of dihydroxybenzene, and advantageously with efficient recycling of the compounds used.

The invention relates to a process for producing at least one alkoxyhydroxybenzaldehyde ("AHBA") from at least one hydroxyphenol ("HP"), said process comprising the formation of at least one alkoxyphenol ("AP") and of alkylalkoxyphenol ("AAP") and the separation (S) of AP from AAP, said separation (S) being carried out prior to obtaining AHBA.

Owing to their structure, AAHBA and AHBA have similar physical characteristics, including in particular similar boiling points. Those skilled in the art therefore typically separate these compounds by crystallization. It would be very difficult to envision a separation of these products by distillation, mainly because of the proximity of the boiling points.

The inventors have noted that it is possible to provide a process for purifying AHBA prepared from HP while solving the abovementioned problems.

The present invention makes it possible in particular to limit the formation of the alkylated impurity, and more particularly to limit the presence of the compound of the alkylalkoxyhydroxybenzaldehyde type during the production of at least one alkoxyhydroxybenzaldehyde compound, for instance 5-methyl-vanillin or 5-ethyl-ethylvanillin during the production of vanillin and/or of ethylvanillin.

The present invention also makes it possible to remove the dialkoxylated impurity also formed, and in particular veratrole during the production of vanillin.

The synthesis of alkoxyphenol from hydroxyphenol is known, whether in the vapor phase or in a three-phase medium.

The inventors have in particular discovered that, in the vapor phase, the formation of impurities of the alkylalkoxyhydroxybenzaldehyde type is limited during the production of at least one alkoxyhydroxybenzaldehyde compound if a separation is carried out prior to obtaining the alkoxyhydroxybenzaldehyde.

DETAILED DESCRIPTION OF THE INVENTION

The process of the invention applies quite particularly to the production of vanillin and of ethylvanillin, but it is also suitable for other aromatic aldehydes. The process of the invention also applies to the production of guaiacol and/or of guaethol from pyrocatechol, but it is also suitable for other alkoxyphenols.

The term "hydroxyphenol" is intended to mean at least one compound of benzene type, which is substituted or unsubstituted, comprising two hydroxyl groups. The hydroxyphenol may be substituted, for example, with one or more groups selected from: hydroxyl, alkyl, alkoxy, halogen, nitro and aryl, the groups comprising carbon atoms possibly comprising one or more heteroatoms, in particular selected from O, N and S. It corresponds more particularly to formula (I) below:

in said formula (I):
the $R_1$ group(s), which may be identical or different, represent a hydrogen atom, a hydroxyl group, or an alkyl or alkoxy group;
n is an integer from 0 to 3.

The respective position of the two hydroxyl groups of formula (I) is not therefore fixed. They may be in the ortho, meta or para position.

Among the compounds of formula (I), mention may be made of pyrocatechol ("PC" or ortho-hydroxyphenol), resorcin ("RS" or meta-hydroxyphenol) and hydroquinone ("HQ" or para-hydroxyphenol), which are preferred for the process according to the invention.

In the context of the invention, the term "alkyl" is intended to mean a linear or branched hydrocarbon-based chain having from 1 to 12 carbon atoms and preferably from 1 to 4 carbon atoms. Preferred examples of alkyl groups are methyl, ethyl, propyl, isopropyl and tert-butyl groups.

The term "alkoxy" is intended to mean an —O-alkyl group in which the term "alkyl" has the meaning given above. Preferred examples of alkoxy groups are methoxy and ethoxy groups.

With the term "alkoxyphenol" (AP), the invention covers an alkoxyphenol compound alone or a mixture of alkoxyphenols. With the term "G", the invention covers guaiacol (GA), guaethol (GE) and any mixture thereof.

The term "alkoxyphenol" is intended to mean at least one compound of benzene type comprising a hydroxyl group and an alkoxy (or O-alkyl) group. It corresponds more particularly to the formula (II) below:

in said formula (II):
R represents an alkyl group, preferably comprising from 1 to 4 carbon atoms, covalently bonded to the oxygen atom;
$R_1$ and n are as defined above with reference to the compound of formula (I).

The alkoxyphenol compounds are produced from the corresponding hydroxyphenol compound, i.e. the R group, provided by an O-alkylating agent, replaces a hydrogen of one of the hydroxyl groups of the starting hydroxyphenol compound.

Mention may in particular be made of guaiacol, guaethol, para-methoxyphenol (PMP) and para-ethoxyphenol (PEP).

With the term "alkoxyhydroxybenzaldehyde" (AHBA), the invention covers an alkoxyhydroxybenzaldehyde compound alone or a mixture of alkoxyhydroxybenzaldehydes.

The term "alkoxyhydroxybenzaldehyde" is intended to mean at least one compound of phenyl type comprising a hydroxyl group, an alkoxy (or O-alkyl) group, and a formyl group. It corresponds more particularly to the formula (III) below:

(III)

R, R₁ and n are as defined above with reference to the compound of formula (I).

The alkoxyhydroxybenzaldehyde preferentially used in the process of the invention corresponds to the formula (III) in which R represents a methyl or ethyl group and n=0.

As more specific examples of alkoxyhydroxybenzaldehyde, mention may in particular be made of:
vanillin,
ethylvanillin (3-ethoxy-4-hydroxybenzaldehyde),
isovanillin (4-methoxy-3-hydroxybenzaldehyde),
o-vanillin (3-methoxy-2-hydroxybenzaldehyde),
syringic aldehyde (3,5-dimethoxy-4-hydroxybenzaldehyde).

In the present invention, when reference is made to the "AHBA" compound, this covers in particular "VA and/or EVA". With the terms "VA and/or EVA", the invention covers vanillin (VA), ethylvanillin (EVA) and any mixture thereof. With the term "V", the invention refers to the compounds VA and/or EVA.

With the term "alkylalkoxyphenol" (AAP), the invention covers an alkylalkoxyphenol compound alone or a mixture of alkylalkoxyphenols. The term "alkylalkoxyphenol" is intended to mean a compound of the type "alkoxyphenol" according to the formula (II) bearing, in addition, an alkyl group on the benzene nucleus. With the term "AG", the invention covers an alkylguaiacol (AGA), and in particular 6-methylguaiacol (MEGA or 2-methoxy-6-methylphenol), an alkylguaethol (AGE), in particular 6-ethylguaethol (EGE or 2-ethoxy-6-ethylphenol), and any mixture thereof.

With the term "alkylalkoxyhydroxybenzaldehyde" (AAHBA), the invention covers an alkylalkoxyhydroxybenzaldehyde compound alone or a mixture of alkylalkoxyhydroxybenzaldehydes. With the term "AV", the invention covers vanillin and/or ethylvanillin comprising an alkyl in position 5 of the phenyl group, and covers in particular 5-methyl-vanillin (MEVA or 4-hydroxy-3-methoxy-5-methylbenzaldehyde) and/or 5-ethyl-ethylvanillin (EEVA or 4-hydroxy-3-ethoxy-5-ethylbenzaldehyde).

Each reference to "AHBA" covers in particular "V". Likewise, each reference to the "AAHBA" impurity covers in particular the "AV" impurity, each reference to "AP" covers in particular "G", and each reference to the "AAHB" impurity covers in particular the "AG" impurities, unless otherwise indicated.

O-Alkylation Reaction

AAHBA is generated mainly during the vapor-phase synthesis of the AP compound from HP, said synthesis comprising, for example, the O-alkylation of a hydroxyl group of HP in the presence of at least one O-alkylating agent bearing at least one alkyl group (referred to herein as HP O-alkylation reaction).

The vapor-phase synthesis of an alkoxyphenol is known according to the prior art. Reference is in particular made to the following patents: EP 0 509 927, EP 0 873 786, EP 914 854 and EP 0 933 107. In accordance with the process of the invention, at least one hydroxyphenol is reacted with an O-alkylating agent, in the vapor phase, optionally in the presence of a catalyst, often in solid form.

The expression "vapor phase" is intended to mean that the various reagents are vaporized under the reaction conditions, but the process does not exclude the presence of a possible very minor liquid phase. The reaction is carried out in the vapor phase, optionally in the presence of solids, such as one or more catalysts. According to one preferred variant, the process of the invention is solely carried out with reagents and products in the vapor phase, it being possible for only the catalyst(s) to be solid or supported on one or more solids.

The organic compounds that can be used for the process of the present invention are hydroxyphenols. In particular, the organic compounds that can be used for the process of the present invention are selected from the aromatic compounds defined by the invention, and preferably catechol, hydroquinone and resorcinol.

The O-alkylating agent may be selected from a compound bearing at least one alkyl group, and preferably bearing at least one methyl, ethyl, propyl, isopropyl, butyl, isobutyl, tert-butyl, amyl, sec-amyl, isoamyl or amyl group, each preferably having a boiling point of from 50 to 200° C., more preferably from 60 to 150° C. Among the O-alkylating agents that can be used in the context of the present invention, mention may particularly be made of alcohols having from 1 to 12 carbon atoms, and preferably $C_1$-$C_4$ alcohols. As examples of O-alkylating agents, mention may be made of lower aliphatic alkanols having from 1 to 5 carbon atoms, for instance methanol, ethanol, trifluoroethanol, propanol, isopropyl alcohol, butanol, pentanol, isopentanol or ethylene glycol monoethyl ether, and also higher aliphatic alcohols having at least 6 and up to 12 carbon atoms, for instance hexanol, heptanol, isoheptanol, octanol, nonanol, decanol or dodecanol. Cycloaliphatic alcohols having from 3 to 12 carbon atoms, for instance cyclopentanol, cyclohexanol, cycloheptanol, cyclooctanol, cyclododécanol, tripropylcyclohexanol, methylcyclohexanol and methylcycloheptanol, can be used. The O-alkylating agent is preferably selected from aliphatic alcohols. The preferred alcohols are methanol, ethanol, isopropanol and tert-butanol, or ethylene glycol. Other O-alkylating agents can be envisioned, such as alkyl halides, including in particular methyl or ethyl chloride; alkyl carbonates, such as methyl carbonate or ethyl carbonate; or alkyl phosphates, such as trimethyl phosphate or triethyl phosphate.

Thus, the present invention covers more particularly the AHBA and AP compounds where the alkoxy is a $C_1$-$C_4$ group, and preferably a methoxy group and/or an ethoxy.

In accordance with the process of the invention, the O-alkylation reaction is carried out in the vapor phase, by bringing the phenolic compound of formula (I) and the O-alkylating agent into contact.

The amount of O-alkylating agent, preferably of alkanol, used is greater than or equal to the stoichiometric amount required to etherify one or more hydroxyl groups to give alkoxy groups. Generally, the O-alkylating agent, preferably the alkanol, is used in an amount such that the ratio between the number of moles of the O-alkylating agent and the number of hydroxyl functions of the phenolic compound of formula (I) ranges between 0.5 and 500, preferably between 2 and 20. According to one variant, the hydroxyphenol and the O-alkylating agent are preferably mixed in a ratio by weight of mixture of from 0.5:99.5 to 90:10, more preferably from 1:99 to 80:20. Advantageously, they are mixed in a ratio by weight of mixture of from 20:80 to 80:20, and more preferably from 30:70 to 70:30.

An O-alkylation reaction catalyst can be used in the production of the alkoxyphenol. A catalyst that can be used is not limited to a specific type of catalyst as long as the catalyst can accelerate the vapor-phase reaction for O-alkylation of the hydroxyphenol by the O-alkylating agent. The catalyst is preferably selected from catalysts containing an alkali metal, for example alkali metal hydroxides, carbonates and bicarbonates; p-toluenesulfonic acid and/or aluminum phosphate catalysts; Al—B—P catalysts; Al—B—P alkaline-earth metal catalysts; Al—B—P—Si catalysts; Al—B—P—Ca catalysts; Al—P—Ti—Si catalysts; and catalysts comprising an active component obtained from boric acid and from phosphoric acid and carried on a vehicle comprising an inert alumina.

For the production of alkoxyphenol from hydroxyphenol, and in particular from pyrocatechol, Al—P catalysts are preferably used. The Al—P catalysts comprise the Al—P—Ti—Si O-alkylation reaction catalysts represented by $Al_aP_bTi_cSi_dO_e$ (in which a, b, c, d and e represent respectively the number of Al, P, Ti, Si, and O atoms, with, as atomic ratios: when a=1, b=1.0 to 1.9, c=0.05 to 0.5, d=0.05 to 0.2 and e=4.1 to 7.0) as described in the nonexamined Japanese patent publication No. 4-341 345. In the production of alkoxyphenol from hydroxyphenol, the abovementioned Al—P—Ti—Si catalyst can be added to a catalyst containing 0.004 to 0.015 sulfur atom per aluminum atom, so as to form a composite catalyst. Mention may also be made of catalysts of the $Al_aP_bTi_cSi_dX_eO_f$ type where X is Bi, Sb, Bi/Sb, or S, with the atomic ratios a:b=1:1.0 to 1:1.9; a:c=1:0.05 to 1:0.5; a:d=1:0.05 to 1:0.2; a:e=1:0.01 to 1:0.3 when X represents at least one Sb or Bi atom, and a:e=1:0.004 to 1:0.015 when X represents S; and a:f=1:4.1 to 1:8.4. Such catalysts are described in patent EP 0 873 786.

With regard to the catalyst, its weight hourly space velocity (whsv) is preferably between 0.1 and 20 $h^{-1}$, preferably between 0.5 and 5 $h^{-1}$, the weight hourly space velocity of a catalyst being defined by the weight ratio between the phenolic compound introduced per hour and the catalyst.

The catalyst may be supported. The support of the catalyst is then preferably a sintered glass when the catalyst is in powder form and preferably a grid when it is in extruded form.

In the process of the present invention where the vapor phase consists of a mixture of several components, the vapor phase is generated by evaporation of a liquid consisting of a mixture comprising at least one hydroxyphenol and at least one O-alkylating agent. The hydroxyphenol and the O-alkylating agent are introduced on contact with the catalyst, optionally entrained by a carrier gas. The carrier gas is optional and is generally a gas or a mixture of gases not reactive under the reaction conditions. Gases such as nitrogen, air, argon or helium may be used. Advantageously, the volume ratio between the carrier gas and the phenolic compound ranges between 0 and 10 and preferably between 0.1 and 2.0.

The reaction pressure may be between $10^{-2}$ and 50 bar, and is preferably atmospheric pressure.

The liquid consisting of a mixture of several components is preferably introduced into an evaporator at a feed temperature of approximately 50 to 300° C., more preferably of 80 to 250° C., even more preferably of 100 to 220° C., so as to prevent or limit the thermal deterioration of the components, especially those having a high boiling point.

It is possible to vaporize each of the reagents (hydroxyphenol, O-alkylating agent, etc) in different chambers, and then to carry out the mixing in a mixing chamber and to introduce the resulting gas stream onto the catalyst. The carrier gas may be introduced in parallel to said gas stream or else at the level of the mixing chamber.

Another variant consists in preparing a solution comprising the hydroxyphenol and the O-alkylating agent, and then in vaporizing said mixture and in introducing it onto the catalyst, in parallel with the carrier gas.

Another practical embodiment of the invention consists in melting the hydroxyphenol by heating it to its melting point, and passing over it a gas stream comprising the O-alkylating agent. This stream becomes saturated with hydroxyphenol and it is then brought into contact with the catalyst.

At the end of the reaction, all of the gases are condensed and the unreacted reagents and the products obtained are separated by distillation.

In the process of the present invention, for example when 100 parts by weight of hydroxyphenol having a boiling point of from 150 to 300° C., particularly from 180 to 290° C., under atmospheric pressure, and 80 to 120 parts by weight of an O-alkylating agent having a boiling point of from 50 to 200° C., particularly from 60 to 150° C., and from 100 to 200° C., particularly from 120 to 180° C., under the boiling point of the hydroxyphenol, are mixed together, the resulting liquid can be vaporized and then injected into a vapor-phase O-alkylation reactor in order to generate the alkoxyphenol (AP) of interest. For further details, reference may in particular be made to the conditions and equipment recommended in patent EP 0 914 854 B1.

The vapor-phase O-alkylation reaction is preferably carried out in a reactor at a temperature of from 200 to 400° C., preferably from 220 to 350° C., and more preferably from 230 to 300° C., under an ambient atmospheric pressure or an increased pressure, for example from 98 to 4903 kPa (1 to 50 kg/cm$^2$), and preferably from 147 to 2942 kPa (1.5 to 30 kg/cm$^2$).

The contact time, which is defined as the ratio between the apparent volume of catalyst and the flow rate of the gas stream (which includes the carrier gas), may vary widely, and is usually between 0.5 and 100 seconds. The contact time is preferably chosen between 1 and 10 seconds. With regard to the practical implementation of the invention, the process begins by preparing the catalytic bed, which consists of the catalyst placed on a support (for example sintered glass or a grid), which allows circulation of the gases without elution of the catalyst. Use is then made of the reagents, and several variants are possible.

The advantage of the process which is the subject of the present invention is that it makes it possible to obtain at least one alkoxyphenol with good reaction selectivity.

The process which is the subject of the present invention is entirely suitable for the production of guaiacol and/or of guaethol by means of a reaction for O-alkylation of pyrocatechol respectively with methanol and/or ethanol.

In the case of the O-methylation of pyrocatechol, the process of the invention is highly advantageous since it makes it possible to modulate the production of guaiacol or of veratrole according to the market needs by controlling the amount of methanol and the pressure (1 and 20 bar).

The same is true for the O-methylation of hydroquinone which makes it possible to obtain p-methoxyphenol and/or p-dimethoxybenzene.

The process of the invention carries out an O-alkylation without using the conventional O-alkylating agents such as methylene chloride which has a certain toxicity. Furthermore, it does not result in saline aqueous effluents, which makes it very advantageous with respect to environmental and economic constraints, since it makes it possible to dispense with treatment of aqueous discharges.

The reaction product delivered from the O-alkylation reactor contains, as target product, the alkoxyphenol, and the alkylalkoxyphenol, as impurity, the unreacted O-alkylating agent, the unreacted hydroxyphenol and by-products. The stream originating from the O-alkylation reactor therefore comprises a mixture M comprising AP and the AAP impurity.

The precursors of the MEVA and EEVA impurities are generated in particular during the vapor-phase production of GA and/or GE from PC by O-alkylation.

It is therefore particularly advantageous to separate AAP from the mixture M, in order to obtain the AP compound separated from the AAP impurity. This separation makes it possible to prepare AHBA substantially free of alkylalkoxyhydroxybenzaldehyde (AAHBA). The term "substantially free" is intended to mean that the amount of AAHBA impurity is sufficiently low to allow the AHBA product produced to be used in the food industry. This amount is preferably less than 1000 ppm and preferably less than 500 ppm, and preferably less than 200 ppm, relative to the alkoxyhydroxybenzaldehyde formed.

According to one variant, the present invention relates to the production of a stream of VA prepared from GA.

According to another variant, the present invention relates to the production of a stream of EVA prepared from GE.

According to another variant, the present invention relates to the production of a stream of a mixture of VA and EVA prepared from a mixture of GA and GE.

The invention relates in particular to a process for purifying a stream of VA and/or EVA, in particular obtained from PC. The invention also relates in particular to the prior separation of the AAP impurity before its conversion to AAHBA, and more particularly of the MEGA or EGE impurity before its conversion to MEVA or EEVA. Thus, the invention covers a process for purifying VA and/or EVA obtained from GA and/or GE, in which the process comprises the separation (S) of MEVA and/or EEVA prior to obtaining VA and/or EVA.

The separation (S) according to the invention makes it possible to obtain the AHBA compound, and in particular VA and/or EVA, highly purified from the viewpoint of the AAHBA impurity (AAHBA less than 100 ppm by weight of the final mixture comprising the AHBA compound), and in particular from the viewpoint of the MEVA or EGE impurity.

According to one variant, the process of the present invention comprises the production of AHBA by reaction of AP with glyoxylic acid, and then oxidation. Advantageously, the separation (S) is carried out before the oxidation of the compound resulting from the reaction of AP with glyoxylic acid. Preferably, the separation is carried out before the reaction of AP with glyoxylic acid. Thus, it is preferred to separate AAP as early as possible after its formation during the synthesis of AHBA from HP.

As indicated above, distillation of the VA/MEVA and/or EVA/EEVA mixture is very difficult. This is all the truer for the distillation of a GA/MEGA and/or GE/EGE mixture since the boiling points are even closer.

It has been discovered, fortuitously, that it is possible to separate GA from MEGA by distillation, and therefore more generally to separate G from AG.

The separation (S) is therefore advantageously carried out by implementing one or more distillation steps. Reference is made in the invention to distillation independently of whether it comprises one or more distillation steps.

In the presence of PC, PC influences the distillation mixture, comprising G and AG, such that it becomes possible to collect AG at the bottom of the distillation column with PC, whereas G is collected at the top.

Unless otherwise indicated, for the purposes of the invention, the term "(distillation) column" is intended to mean in particular distillation equipment comprising (i) a cylindrical device forming a distillation column, generally equipped (ii) in its lower part with a heating device called a boiler, preferably also comprising a device for drawing off a "column bottom" stream or fraction, and preferably comprising a device for reintroducing, into the lower part of the column, at least one part of the vaporized falling liquid, and (iii) in its upper part with a drawing off device, optionally equipped with a liquid-vapor separation device called a condenser, making it possible to draw off a gas stream termed column top stream or fraction, optionally partially or totally condensed in liquid form, and preferably also comprising a device for reintroducing, into the upper part of the column, at least one part of the condensed liquid. The term "column bottom" is also used to refer to the lower part of the column and the term "column top" is also used to refer to the upper part of the column. According to one preferred variant, the boiler is a falling liquid film boiler.

The dialkoxylated HP compound (DAB or dialkoxybenzene) it is also an impurity of the process for producing V from HP. These compounds are typically veratrole (VER or 1,2-dimethoxybenzene) and 1,2-diethoxybenzene. DAB has a higher boiling point than AG, and DAB should prevent AG from being collected at the column bottom.

Completely surprisingly and contrary to what the inventors were expecting, when DAB is present in the stream to be separated, i.e. the stream comprising G, AG and PC, PC influences in particular the A/G, DAB/G and AG/G relative volatilities.

More specifically, the DAB/G and AG/G relative volatilities can be inverted in particular at the column top compared with the column bottom in the presence of PC, which makes it possible to collect a highly purified stream of G with a very low concentration of AG, which can be less than 1000 ppm, preferably less than 500 ppm, preferably less than 200 ppm and more advantageously less than 100 ppm. If PC was not present, veratrole would exhibit, at the column bottom, a relative volatility with respect to GA that is lower than the relative volatility of MEGA/GA, and veratrole would behave like a compound that is "heavier" than MEGA, the latter therefore passing more readily with GA. However, surprisingly, in the presence of PC, the relative volatilities at the column bottom are inverted and MEGA passes preferentially, with respect to veratrole, at the column bottom, with the stream containing PC. The invention therefore covers in particular a process comprising a distillation in which the concentration of veratrole collected with GA at the top is greater than the concentration of MEGA collected with GA at the top, PC being collected at the bottom.

The distillation conditions are selected so that they impose such an inversion of the relative volatilities. It is preferable for the stream entering the distillation column to comprise at least 30% by weight of PC relative to the total weight of the stream, and preferably at least 35%, and more preferably at least 40% by weight.

Advantageously, the process of the invention comprises the production of VA and/or EVA, substantially free of 5-methylvanillin ("MEVA") and of 3-ethoxy-5-ethyl-4-hydroxybenzaldehyde ("EEVA"), from guaiacol (GA) and/or from guaethol (GE), said process comprising the obtaining of a mixture (M) comprising GA and/or GE in the presence of the impurity 6-methylguaiacol ("MEGA") and/or 6-ethylguaethol (2-ethoxy-6-ethylphenol termed "EGE"), said process comprising the separation (S) of GA and/or GE from MEGA and/or EGE, said separation (S) being carried out prior to obtaining VA and/or EVA.

According to one variant of the invention, the AHBA compound is produced by addition of an aldehyde function to the AP compound by condensation with glyoxylic acid, then oxidation of the resulting compound, and the separation (S) is carried out before the oxidation to give the AHBA compound.

According to another variant of the invention, the separation is carried out before the reaction of AP with glyoxylic acid.

These different variants can be combined with one another.

Advantageously, the separation is carried out by implementing one or more distillation steps.

According to the process of the invention, the distillation can be carried out continuously or batchwise, but preferably continuously. According to the invention, the distillation column can be adapted to the desired degree of purity, and it can consist of materials suitable for the acidic conditions of the mixture to be distilled.

Preferably, the process of the invention comprises the introduction of a stream or fraction (E1) of the mixture M comprising GA and/or GE, denoted "G", and MEGA and/or EGE, denoted "AG", in the presence of pyrocatechol (PC) in a distillation column (E), and the recovery of G essentially at the top of the distillation column in a stream or fraction (E2) and of PC and AG essentially at the bottom of the distillation column in a stream or fraction (E3).

According to one variant, said mixture M also comprises a dialkoxybenzaldehyde (DAB), DAB being in particular veratrole (VER), and the DAB compound is recovered essentially at the bottom of the distillation column in the stream or fraction (E3).

According to one embodiment, PC represents from 25% to 75%, and preferably from 35% to 65%, and more preferably from 40% to 45%, by weight of the total weight of the stream or fraction (E1).

According to one embodiment, G represents from 25% to 75%, and preferably from 35% to 65%, and more preferably from 45% to 50%, by weight of the total weight of the stream or fraction (E1).

According to one embodiment, G represents more than 90%, and preferably more than 95%, and more preferably more than 99%, by weight of the total weight of the stream or fraction (E2), and it is preferably characterized in that AG represents less than 1%, and preferably less 0.5%, and more preferably less than 0.2%, by weight relative to the total weight of the stream or fraction (E2).

Advantageously, the stream or fraction (E2) comprises from 90% to 100%, and preferably from 95% to 100%, and more preferably from 99% to 100% of G, from 0 to 1%, and preferably less than 0.5%, and more preferably less than 0.2% of AG, and from 0 to 1%, and preferably less than 0.5%, and more preferably less than 0.2% of VER, the percentages being expressed by weight relative to the total weight of the stream or fraction (E2).

Advantageously, PC represents more than 60%, and preferably more than 70%, and more preferably more than 75%, by weight of the total weight of the stream or fraction (E3), and preferably AG represents less than 8%, and preferably less than 5%, and more preferably less than 3%, by weight relative to the total weight of the stream or fraction (E3).

Preferably, the stream or fraction (E3) comprises from 60% to 100%, and preferably from 70% to 100%, and more preferably from 75% to 100% of PC, from 0 to 8%, and preferably less than 5%, and more preferably less than 3% of AG, and from 0 to 10%, and preferably less than 8%, and more preferably less than 5% of VER, the percentages being expressed by weight relative to the total weight of the stream or fraction (E3).

The invention also relates to a process for separating GA and/or GE from a mixture (M) comprising GA and/or GE and a 6-methylguaiacol ("MEGA") and/or 6-ethylguaethol (2-ethoxy-6-ethylphenol termed "EGE") impurity, in which the mixture M is introduced into a distillation column in the presence of pyrocatechol (PC), and a stream or fraction comprising GA and/or GE is recovered at the top of the distillation column and a stream or fraction comprising PC, MEGA and/or EGE is recovered at the bottom of the distillation column.

The invention also relates to a process for synthesizing at least one alkoxyphenol termed "AP" in the vapor phase, comprising the formation of at least one AP on the basis of a reaction, termed O-alkylation reaction, in the vapor phase, between at least one hydroxyphenol termed "HP" and at least one O-alkylating agent, said reaction also forming at least one alkylalkoxyphenol impurity termed "AAP", said reaction thus forming a mixture M comprising AP, AAP and HP, said process comprising the introduction of the mixture M into at least one distillation column and the recovery of a stream or fraction AP at the top of the distillation column and of a stream or fraction comprising HP and AAP at the bottom of the distillation column, said process optionally comprising a recycling of the stream or fraction comprising AP downstream of the O-alkylation reaction and/or a recycling of the stream or fraction comprising HP upstream of the O-alkylation reaction.

Advantageously, the process comprises the formation of at least guaiacol (GA) and/or guaethol (GE) on the basis of a reaction, termed O-alkylation reaction, in the vapor phase, between pyrocatechol termed "PC" and at least one O-alkylating agent, said reaction also forming at least one 6-methylguaiacol ("MEGA") and/or 6-ethylguaethol (2-ethoxy-6-ethylphenol termed "EGE") impurity, said reaction thus forming a mixture M comprising GA and/or GE, MEGA and/or EGE, and PC, said process comprising the introduction of the mixture M into at least one distillation column and the recovery of a stream or fraction comprising GA and/or GE at the top of the distillation column and of a stream or fraction comprising PC and MEGA and/or EGE at the bottom of the distillation column, said process optionally comprising a recycling of the stream or fraction comprising GA and/or GE downstream of the O-alkylation reaction and/or a recycling of the stream or fraction comprising PC upstream of the O-alkylation reaction.

Preferably, the distillation in the column (E) is carried out at a temperature of between 80 and 200° C. More specifically, it is preferred to maintain a temperature of between 120 and 180° C. at the bottom of the column. It is preferred to maintain a temperature of from 80 to 120° C. at the top of the column. In the context of the invention, and unless otherwise mentioned, the temperature at the bottom of the distillation column corresponds to the temperature in the boiler.

According to one embodiment, the distillation in the column (E) is carried out at atmospheric pressure. Preferably, the distillation is carried out under partial vacuum, and preferably in particular at a pressure ranging from 1 to 300 mbar (0.1 to 30 kPa), preferably from 15 to 100 mbar (1.5 to 10 kPa).

According to one embodiment, the column (E) comprises from 12 to 70 theoretical plates, and preferably between 20 and 60 theoretical plates. The stream or fraction (E1) is preferably fed at the level of a theoretical plate located between 5% and 70%, and preferably between 10% and 60%, of the total number of theoretical plates of the distillation column (E). Advantageously, the introduction of the feed stream (E1) is carried out in the central part of the column between theoretical plates No. 12 and No. 40, and preferably between theoretical plates No. 15 and No. 30.

According to one embodiment, the distillation in the column (E) is carried out a reflux ratio of between 1 and 10, and preferably between 2 and 8.

The invention also covers a process for purifying GA and/or GE obtained from PC. In particular, this process comprises a separation (S) step as described above, according to any one of the embodiment variants, for separating the AG impurity from G obtained.

The process according to the invention also enables the recycling of PC, in particular following the step of separation (S) by distillation.

Moreover, following the separation of the AAP impurity from the mixture M, the stream or fraction (E3) comprising PC drawn off at the bottom of the column (E) then comprises AAP as impurity: PC and AAP are therefore present as a mixture in the stream or fraction (E3) at the outlet at the bottom of the distillation column (E). The recycling of PC according to the invention can therefore advantageously comprise a distillation of PC in order to separate PC from the AAP impurity. The invention seeks, moreover, to remove the AG impurity contained in a stream or fraction containing PC, since the AG impurity can result in the obtaining of various toxic derivatives.

This separation is difficult. The invention therefore relates to a process for separating AG from a mixture containing AG and PC.

It is especially particularly difficult to obtain PC in the presence of less than 4%, and preferably less than 1%, of AG by weight relative to the total weight of PC.

To obtain PC with such a purity from the viewpoint of AG (typically MEGA), it has been noted that it is necessary to carry out an additional distillation, in a column (F), of the stream or fraction from the bottom of the distillation column (E). Generally, this stream or fraction (E3) from the outlet of the distillation column (E) also comprises the DAB impurity (VER and/or 1,2-diethoxybenzene), which is also difficult to separate from PC. The invention aims to provide a stream or fraction (F6) containing PC with less than 10%, and preferably less than 8%, by total weight of AG and DAB impurities relative to the total weight of PC.

To this effect, it is recommended to advantageously carry out at least one distillation with the stream or fraction (F6) containing the largest amount of PC being drawn off at the side. According to one advantageous embodiment, the process therefore comprises an additional distillation, in a column (F), of the stream or fraction (E3) from the bottom of the distillation column (E) by drawing off a stream or fraction (F6) at the side of the column (F) so as to draw off a stream or fraction enriched with PC. An absence of drawing off at the side would result in particular in an unwanted amount of DAB and/or of AG in the stream or fraction drawn off containing predominantly PC. This implementation makes it possible to draw off a stream or fraction (F4) at the top of the column (F) also comprising predominantly PC, and G, DAB and AG residues. The stream or fraction (F5) from the bottom of the column (F) essentially comprises tars. The stream or fraction (F4) can again be fractionated in a distillation column (F2) so as to collect a stream or fraction (F7) at the bottom of the column (F2), containing PC and where G, DAB and AG are present in an amount by weight that is at most half the amount in the stream (F4), and to collect a stream or fraction (F8) at the top of the column (F2) comprising predominantly G, DAB and AG. Advantageously, the stream or fraction (F7) containing PC is mixed with the stream or fraction (F6) so as to advantageously recycle them to the PC alkylation reaction. Advantageously, the stream or fraction at the top of the column (F2) can be mixed with the stream or fraction (E1) entering the distillation column (E) so as to carry out the recycling thereof.

Preferably, the distillation in the column (F) is carried out at a temperature of between 120 and 250° C. More specifically, it is preferred to maintain a temperature of between 180 and 220° C. at the bottom of the column. It is preferred to maintain a temperature of from 120 to 180° C. at the top of the column.

According to one embodiment, the distillation in the column (F) is carried out at atmospheric pressure. Preferably, the distillation is carried out under partial vacuum, and preferably in particular at a pressure ranging from 1 to 300 mbar (0.1 to 30 kPa), preferably from 15 to 100 mbar (1.5 to 10 kPa).

According to one embodiment, the column (F) comprises from 8 to 50 theoretical plates, and preferably between 10 and 40 theoretical plates. The stream or fraction (F1) is preferably fed at the level of a theoretical plate located between 5% and 70%, and preferably between 10% and 60%, of the total number of theoretical plates of the distillation column (F). Advantageously, the introduction of the feed stream (F1) is carried out in the central part of the column between theoretical plates No. 2 and No. 20, and preferably between theoretical plates No. 5 and No. 20.

According to one embodiment, the distillation in the column (F) is carried out at a reflux ratio of between 1 and 10, and preferably between 1 and 8.

Preferably, the distillation in the column (F2) is carried out at a temperature of between 80 and 200° C. More specifically, it is preferred to maintain a temperature of between 120 and 180° C. at the bottom of the column. It is preferred to maintain a temperature of from 80 to 140° C. at the top of the column.

According to one embodiment, the distillation in the column (F2) is carried out at atmospheric pressure. Preferably, the distillation is carried out under partial vacuum, and preferably in particular at a pressure ranging from 1 to 300 mbar (0.1 to 30 kPa), preferably from 15 to 100 mbar (1.5 to 10 kPa).

According to one embodiment, the column (F2) comprises from 1 to 20 theoretical plates, and preferably between 2 and 10 theoretical plates. The stream or fraction (F4) is preferably fed at the level of a theoretical plate located between 5% and 70%, and preferably between 10% and 60%, of the total number of theoretical plates of the distillation column (F2). Advantageously, the introduction of the feed stream (F4) is carried out in the central part of the column between theoretical plates No. 1 and No. 15, and preferably between theoretical plates No. 2 and No. 10.

According to one embodiment, the distillation in the column (F2) is carried out at a reflux ratio of between 1 and 10, and preferably between 2 and 8.

According to one particular embodiment, the distillation comprises, beforehand, a separation, preferably by distillation in a column (A), of the lightest compounds from the heaviest compounds so as to draw off, at the top of the column (A), a stream or fraction (A1) containing the light compounds and, at the bottom of the column (A), a stream or fraction (A2) containing the heavy compounds including AP. This separation makes it possible in particular to remove the O-alkylating agent that has not reacted during the reaction with HP, and in particular PC. According to one variant, the stream or fraction (A2) is used as the stream entering the distillation column (E), referred to above as stream or fraction (E1).

Preferably, the distillation in the column (A) is carried out at a temperature of between 80 and 250° C. More specifically, it is preferred to maintain a temperature of between 130 and 220° C. at the bottom of the column. It is preferred to maintain a temperature of from 80 to 150° C. at the top of the column.

According to one embodiment, the distillation in the column (A) is carried out at atmospheric pressure. Preferably, the distillation is carried out under partial vacuum, and preferably in particular at a pressure ranging from 1 to 300 mbar (0.1 to 30 kPa), preferably from 15 to 100 mbar (1.5 to 10 kPa).

According to one embodiment, the column (A) comprises from 8 to 50 theoretical plates, and preferably between 10 and 40 theoretical plates. The stream or fraction (A1) is preferably fed at the level of a theoretical plate located between 5% and 70%, and preferably between 10% and 60%, of the total number of theoretical plates of the distillation column (A). Advantageously, the introduction of the feed stream (A1) is carried out in the central part of the column between theoretical plates No. 2 and No. 20, and preferably between theoretical plates No. 5 and No. 20.

According to one embodiment, the distillation in the column (A) is carried out at a reflux ratio of between 0.01 and 10, and preferably between 0.1 and 5.

The columns can subsequently be proportioned according to the general knowledge of those skilled in the art.

The invention also covers the production of at least one alkoxyhydroxybenzaldehyde from hydroxyphenol.

Synthesis of Alkoxyhydroxybenzaldehyde

The process according to the invention makes it possible to produce an alkoxyhydroxybenzaldehyde by adding an aldehyde function to the abovementioned alkoxyphenol compound.

The process according to the invention makes it possible to produce in particular vanillin and/or ethylvanillin from guaiacol and/or guaethol, in particular from guaiacol and/or guaethol purified according to the process of the invention. The guaiacol/guaethol mixture is obtained in any proportions. The GA/GE ratio depends on the O-alkylation conditions. This GA/GE weight ratio may, for example, range from 0.1/100 to 100/1. The vanillin/ethylvanillin weight ratio preferably ranges from 80/20 to 40/60, or preferably from 80/20 to 45/55. According to one variant, the vanillin/ethylvanillin molar ratio is at least equal to 2. Preferably, the proportion of vanillin by weight is between 65% and 72%, and preferably between 60% and 70%, and the proportion of ethylvanillin is between 28% and 35%, and preferably between 30% and 33% by weight.

Reference is made to the alkoxyphenol, guaiacol and guaethol compounds, and to the corresponding alkoxyhydroxybenzaldehydes independently of their salified or nonsalified form. When reference is explicitly made to the salt, this makes it possible to describe a particular detail regarding this aspect. Those skilled in the art are able to know when they are in the presence of the salified or nonsalified compound, in particular in the light of the cited literature and of their general knowledge.

The aldehyde function is advantageously provided according to two main reactions, namely a condensation of the alkoxyphenol compound with glyoxylic acid and the oxidation of the compound resulting from the condensation reaction.

According to one preferred embodiment, the process of the invention also comprises the following steps:
condensation of the alkoxyphenol compound with glyoxylic acid so as to obtain the corresponding mandelic compound;
separation of the alkoxyphenol compound from the solution containing the mandelic compound, preferably with recycling of the alkoxyphenol compound;
oxidation of the mandelic compound so as to obtain the alkoxyhydroxybenzaldehyde;
separation of the alkoxyhydroxybenzaldehyde by extraction with an organic solvent, then separation of the alkoxyhydroxybenzaldehyde from the organic solvent, preferably with recycling of the alkoxyhydroxybenzaldehyde extraction organic solvent, and
recovery of the alkoxyhydroxybenzaldehyde optionally in solid form.

When "mandelic", "vanillin" or "ethylvanillin" is mentioned without further information, the para-mandelic compound, para-vanillin or ethyl-para-vanillin is respectively targeted, unless otherwise indicated.

The para-mandelic compounds (formula (IV)), in particular the production of para-vanillin, have the following formulae:

(IV)

mandelic compound of para-vanillin

Preferably, the steps and their sequence are carried out continuously, with the exception of a few steps such as during the separation of the compounds.

The reactions for condensation of the alkoxyphenols, and in particular of guaiacol, with glyoxylic acid are described in the literature. Mention will quite particularly be made of patents EP 0 578 550, WO 99/65853 and WO 09077383, to which reference is made for the production of the compounds of the invention.

The sequence of the above steps can be carried out according to the following reactions according to the example guaiacol:

Condensation of guaiacol and of glyoxylic acid so as to form para-mandelic acid:

guaiacol+glyoxylic acid+NaOH→guaiacolate+mandelate (phenate)+H$_2$O

Acidification so as to recover the unreacted guaiacol:

guaiacolate+mandelate (phenate)+H$_2$SO$_4$→guaiacol+ mandelate+Na$_2$SO$_4$

Oxidation of the para-mandelic acid so as to form para-vanillin:

mandelate+NaOH+O$_2$→vanillate+Na$_2$CO$_3$+H$_2$O

Acidification so as to form vanillin:

During the separation of the mixture, whether it is of the alkoxyphenol or of the alkoxyhydroxybenzaldehyde, having resulted in their formation, a recycling, also called a loop, is preferably carried out. Thus, in the present invention, reference is made to "recycling loop 1" when referring to the recycling of the excess alkoxyphenol during the condensation reaction, and to "recycling loop 2" when referring to the recycling of the alkoxyhydroxybenzaldehyde extraction solvent, during the separation steps.

Once separated, the alkoxyhydroxybenzaldehyde may be treated so as to obtain it in solid purified form; reference is made in the present invention to "solid chain". This treatment can typically implement the steps of crystallization, pulling dry, and drying, or flaking. Among these steps, some, like the pulling dry, may not be carried out continuously. Thus, the process is preferably continuous, with the exclusion of the pulling dry.

The vanillin and/or the ethylvanillin thus obtained may in particular be used as a flavoring in industry, for instance in the food, pharmaceutical or cosmetics industry, in particular for example for manufacturing fragrances.

The vanillin and/or the ethylvanillin may also be used as a synthesis intermediate, for example for the production of veratric aldehyde (3,4-dimethoxybenzaldehyde) and/or 3,4-diethoxybenzaldehyde.

In this context, if the process relates to the simultaneous production of vanillin and of ethylvanillin, it is possible either to synthesize the vanillin and ethylvanillin according to the same stream, from a stream comprising guaiacol and guaethol, themselves prepared from catechol by simultaneous reaction with an O-methylating agent and an O-ethylating agent; or to synthesize guaiacol and guaethol separately and then to mix them before the condensation step so as to synthesize the vanillin and ethylvanillin according to the same stream; or to synthesize the mandelic compounds separately via separate reactions of the guaiacol and of the guaethol with glyoxylic acid and then to mix the corresponding mandelic compounds before the oxidation step; or to synthesize the vanillin and ethylvanillin separately and then to mix them, for example before the crystallization.

Figure 3:
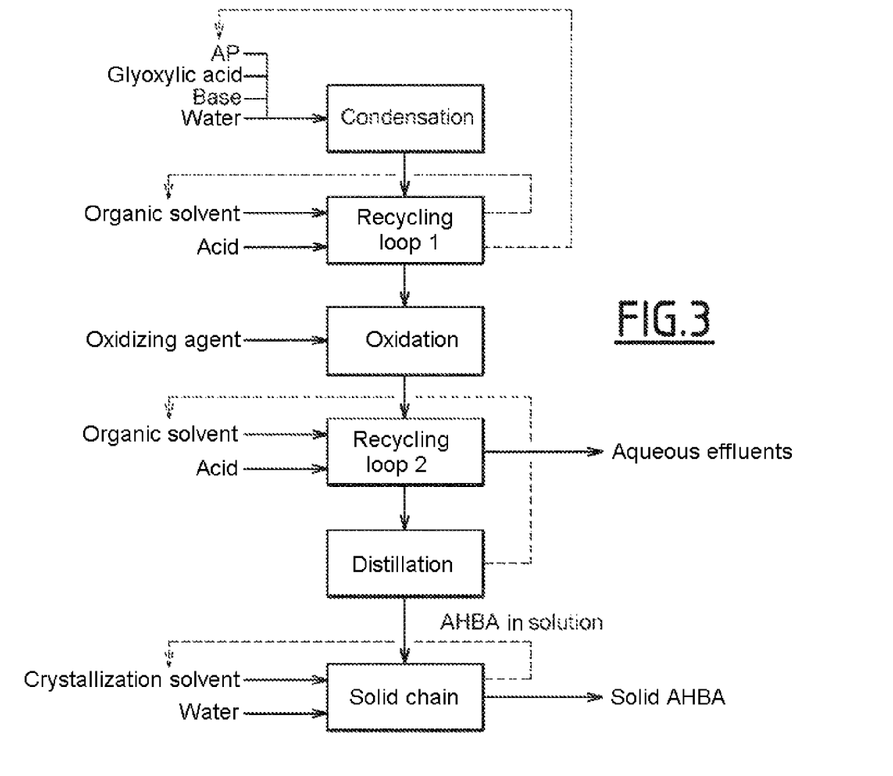
FIGS. 3 and 4 show flow charts according to one or more embodiments.

Thus, it is possible to represent a scheme of the process according to FIG. 3 which advantageously comprises the following steps, after obtaining AP according to the invention:
condensation of the alkoxyphenol (AP) compound with glyoxylic acid so as to obtain the corresponding mandelic compound, after the addition of water, of glyoxylic acid and of a base;
separation of the alkoxyphenol compound from the solution containing the corresponding mandelic compound, after the addition of an organic solvent and of an acid, preferably with recycling of the alkoxyphenol compound;
oxidation of the mandelic compound by reaction with an oxidizing agent introduced so as to obtain the corresponding alkoxyhydroxybenzaldehyde;
separation of the alkoxyhydroxybenzaldehyde by extraction after the addition of an organic solvent and of an acid;
separation of the alkoxyhydroxybenzaldehyde from the organic solvent by distillation, preferably with recycling of the organic solvent; and
recovery of the alkoxyhydroxybenzaldehyde (AHBA), optionally in solid form.

Condensation Reaction

According to one advantageous variant, the alkoxyphenol is reacted with glyoxylic acid in the presence of an inorganic base and of an organic base, and preferably NaOH or KOH, and more preferably in the presence of sodium hydroxide (NaOH), or ammonium hydroxide. According to this variant, a mixture of alkyl phenolate and of derivative of the mandelate type is obtained.

The condensation reaction between the alkoxyphenol (in phenolate form) and glyoxylic acid allows the synthesis of the corresponding para-mandelic acid.

The condensation can be carried out in a cascade of stirred reactors. According to one variant, the reaction is carried out in a piston flow reactor, optionally comprising a heat exchanger. Such an embodiment is, for example, described for guaiacol in application WO 09/077383. The condensation reaction between the alkoxyphenol and glyoxylic acid can be carried out in water, in the presence of an alkali metal, said reaction being carried out in a piston flow reactor. It can be carried out in a tubular reactor.

The condensation reaction can advantageously be catalyzed by a quaternary ammonium hydroxide, for instance according to the reaction described in patent application EP 0 578 550.

The condensation reaction can advantageously be carried out in the presence of a dicarboxylic acid, for instance according to the reaction described in patent application WO 99/65853.

Since the alkoxyphenol is usually in excess with respect to the glyoxylic acid, the alkoxyphenol fraction which has not reacted is advantageously recovered from recycling loop 1. This excess reduces the probability of forming compounds of the dimandelic acid type (i.e. compounds resulting from the condensation of two glyoxylic acid molecules with one guaiacol molecule).

Advantageously, firstly, the alkoxyphenol and sodium hydroxide react to form sodium alkoxyphenolate. For example for guaiacol:

Then the alkoxyphenolate reacts with glyoxylic acid to form the corresponding para-mandelate:

These two reactions for preparing the glyoxylate and the guaiacolate can be carried out according to two separate steps. Alternatively, the glyoxylic acid is brought into contact directly with the guaiacolate in the presence of the base.

Alkoxyphenolate Solution

According to one advantageous variant, an alkoxyphenolate solution is prepared. This alkoxyphenolate solution is fed with alkoxyphenol from a storage tank which receives the alkoxyphenol recycled from recycling loop 1 and the new alkoxyphenol. This alkoxyphenolate solution is advantageously introduced into the reactor for the condensation reaction.

All of the (demineralized) water and of an inorganic base (for example sodium hydroxide) required for the reaction are fed into the alkoxyphenolate solution.

The temperature of the reactor for preparing the alkoxyphenolate solution is advantageously maintained at the condensation reaction temperature.

Recycling Loop 1

Recycling loop 1 is the recovery of the alkoxyphenol which has not reacted in the condensation reaction. Thus, loop 1 relates to the separation of the alkoxyphenol compound from the mandelic compounds, which advantageously comprises the following steps:

recovery of a mixture comprising the mandelic compound formed in mandelate form and the unreacted alkoxyphenol in alkoxyphenolate form;

neutralization of the alkoxyphenolate to give the alkoxyphenol, while maintaining the corresponding mandelate in conjugated base (salified) form;

separation of the alkoxyphenol from the mandelate;

introduction of the mandelate into an oxidation reactor; and recycling of the alkoxyphenol, which has not reacted as a reagent, to the condensation reaction.

The reaction medium resulting from the condensation is advantageously neutralized with an inorganic acid, and preferably with sulfuric acid, so as to convert the unreacted alkoxyphenolate into alkoxyphenol under conditions which keep the mandelate in salified form.

The unreacted alkoxyphenol, present in the organic phase, can be separated from the mandelate formed, present in the aqueous phase.

According to one variant, the alkoxyphenol obtained after neutralization can be extracted by extraction via the addition of an organic solvent which solubilizes the alkoxyphenol contained in the aqueous phase. Reference is made here, for example, to the process described for guaiacol in patent FR 2 379 501.

According to one preferred embodiment, the alkoxyphenol contained in the aqueous phase is extracted with an organic solvent. Use is made of an organic solvent which is inert with respect to the mandelate. As solvents which can be used, mention may in particular be made of halogenated or nonhalogenated aliphatic, cycloaliphatic or aromatic hydrocarbons; alcohols; ethers; ketones and nitriles. As aliphatic, cycloaliphatic or aromatic hydrocarbons, mention is more particularly made of heptane, cyclohexane, methylcyclohexane, benzene and toluene; as halogenated aliphatic, cycloaliphatic or aromatic hydrocarbons, mention is more particularly made of dichloromethane, trichloromethane, dichloroethane, chlorobenzene and dichlorobenzenes; as alcohols, mention is more particularly made of methanol, ethanol, propanol, isopropanol and butanol; as ethers, mention is more particularly made of diethyl ether, diisopropyl ether and methyl (tert-butyl) ether; as ketones, mention is more particularly made of acetone, methyl ethyl ketone, methyl isobutyl ketone, diisobutyl ketone and methyl isobutyl ketone; and as nitriles, mention is more particularly made of acetonitrile. A mixture of said solvents may be used. A solvent of food quality may be used.

The mandelate then remains in the aqueous phase, whereas the alkoxyphenol goes into the organic phase.

The alkoxyphenol to be recycled may be contaminated by the presence of organic solvent residues. The presence of organic solvent in the alkoxyphenol results in a significant decrease in the performance levels of the condensation reaction. It is therefore preferable to separate the extraction solvent from the alkoxyphenol before its reintroduction into the alkoxyphenol storage tank.

After separation of the aqueous and organic phases, the alkoxyphenol-organic phase mixture is preferably distilled so as to separate the organic solvent from the alkoxyphenol, and also from tars generally present, in order to recycle the organic solvent. Other types of separation may be envisioned.

The aqueous phase containing the mandelate is preferably treated so as to remove the residual organic solvent, for example by distillation. The mandelate then feeds the oxidation reaction.

According to one variant, the unreacted alkoxyphenolate can be separated using basic anion exchange resins or an adsorbent resulting in selective binding of the alkoxyphenol and in the recovery of an aqueous stream comprising the mandelic compounds in salified form resulting from the condensation reaction. The stream of the alkoxyphenol in salified form (alkoxyphenolate) bound to the resin or the adsorbent can be separated by means of a resin regeneration treatment or a desorption treatment. Such separation methods are in particular described in patent applications WO 09/141280 and WO 11/039331.

The alkoxyphenol which has not reacted during the condensation reaction is preferably recycled to the feed of the alkoxyphenolate solution.

Removal of the Dialkoxybenzene (Called "DAB") Possibly Present

As was indicated above, the O-alkylation reaction also generates a dialkoxybenzene compound. In the process of the invention, the alkoxyphenol obtained after the O-alkylation reaction is therefore in a mixture with a super alkoxylation (dialkoxylation) compound of the dialkoxybenzene type.

It has in particular been discovered by the inventors that, when veratrole (1,2-dimethoxybenzene) is formed, in particular when guaiacol has been prepared from pyrocatechol, the veratrole accumulates in the guaiacol solution owing to the recycling, but also because it does not react during the condensation reaction with glyoxylic acid. The veratrole concentration in the guaiacol storage tank (mixture of new+ recycled) is variable. Since veratrole does not react in the condensation reactions according to the invention, veratrole therefore has a tendency to accumulate in the guaiacol solution and thus reduces the guaiacol titer in the solution injected into the condensation reactor. In the process of the invention, it is sought to limit the veratrole accumulated in the guaiacol or the guaiacolate solution. Thus, according to one preferred embodiment of the invention, the dialkoxybenzene formed is removed. According to one variant of the process of the invention, the veratrole concentration by weight in the solution comprising AP before the condensation reaction is between 0.01% and 25% and preferably between 0.01% and 10%, and more preferably between 0.01% and 5%, and is generally approximately 2%.

The invention therefore relates to an independently patentable process for producing at least one alkoxyhydroxybenzaldehyde compound from at least one hydroxyphenol compound, said process being characterized in that it comprises:

(i)—the synthesis of at least one alkoxyphenol from at least one hydroxyphenol in the presence of at least one O-alkylating agent;
(ii)—the recovery of at least one alkoxyphenol and of impurities, including a dialkylated compound of the dialkoxybenzene type (also called here "DAB");
(iii)—the separation of the dialkoxybenzene from the alkoxyphenol;
(iv)—the condensation of the alkoxyphenol with glyoxylic acid and the obtaining of the corresponding mandelic compound;
(v)—the oxidation of the mandelic compound to give the corresponding alkoxyhydroxybenzaldehyde; and
(vi)—the recovery of the alkoxyhydroxybenzaldehyde optionally in solid form.

In particular, the invention consists of a process for producing at least one alkoxyhydroxybenzaldehyde selected from vanillin (4-hydroxy-3-methoxybenzaldehyde), ethylvanillin (3-ethoxy-4-hydroxybenzaldehyde), and any mixture thereof, from pyrocatechol.

According to one preferred variant, step (i) is carried out in a three-phase medium as described in the invention, including all the variants and embodiments described without any limitation.

According to one preferred embodiment, step (iii) of separation of the dialkoxybenzene from the alkoxyphenol also comprises the preparation of an aqueous solution of alkoxyphenol in salified (phenolate) form, and the separation of the residual dialkoxybenzene from the aqueous mixture comprising the alkoxyphenoate.

Figure 4:
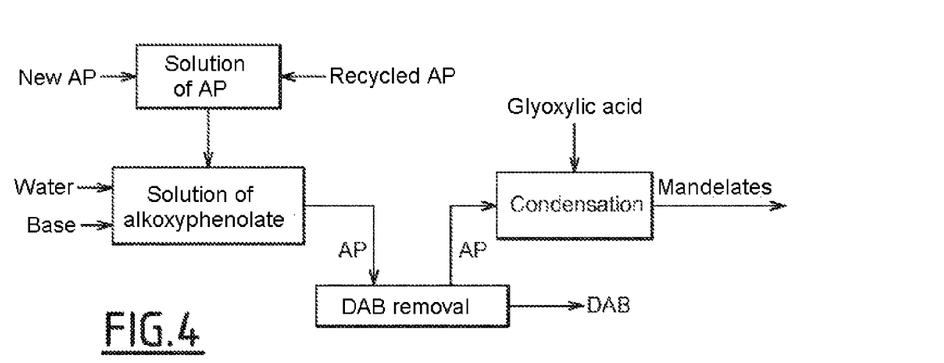

According to one preferred variant, illustrated for example according to FIG. 4, the process comprises the following steps:
  preparation of a solution of alkoxyphenol (AP) for example in a mixture made up of a new alkoxyphenol with an alkoxyphenol originating from recycling, said solution of alkoxyphenol also comprising an impurity of the dialkoxybenzene (DAB) type;
  preparation of a solution of alkoxyphenolate by adding water and at least one base to the solution of alkoxyphenol;
  separation of the dialkoxybenzene from the alkoxyphenol;
  optional exploitation of the dialkoxybenzene;
  condensation of the alkoxyphenol with glyoxylic acid and obtaining of the corresponding mandelic compound, which is for example salified (mandelate).

According to one variant, the separation of the dialkoxybenzene from the alkoxyphenol is carried out by distillation or settling out.

Advantageously, the mandelic compounds are obtained in salified form. Thus, the process of the invention comprises a step of neutralization of the salified mandelic compound to give the mandelic compound in acid form.

According to one variant, the hydroxyphenol is pyrocatechol, the alkoxyphenol is the guaiacol obtained in step (i) with a methylating agent, and the dialkoxybenzene is veratrole, and the process also comprises the separation, in step (iii), of the pyrocatechol from the guaiacol and veratrole mixture.

According to one variant, the hydroxyphenol is pyrocatechol, the alkoxyphenol is the guaethol obtained in step (i) with an ethylating agent, and the dialkoxybenzene is 1,2-diethoxybenzene, and the process also comprises the separation, in step (iii), of the pyrocatechol from the guaethol and 1,2-diethoxybenzene mixture.

Advantageously, a part of the alkoxyphenol(alkoxyphenolate) is advantageously diverted to a distillation column intended to limit the dialkoxybenzene content in the guaiacol before the condensation reaction. The dialkoxybenzene is distilled at the top in the form of a dialkoxybenzene-water heteroazeotrope. A temperature at the bottom of the distillation column of between 90 and 120° C. is preferred. This process makes it possible, for example for guaiacol, to limit the veratrole concentration by weight to 0.01% in the guaiacol (or guaiacolate) used for the condensation reaction.

The dialkoxybenzene-water heteroazeotrope is then advantageously separated by settling out or another means of separation.

The bottom of the column (comprising the alkoxyphenolate) is preferably directed to the feed of the condensation reactor so as to cause the alkoxyphenol (alkoxyphenolate) and the glyoxylic acid to react by condensation.

Oxidation of the Mandelic Compounds to Give Alkoxyhydroxybenzaldehyde

The oxidation step allows the conversion of the mandelic compounds into the desired alkoxyhydroxybenzaldehydes. The para-mandelic compound corresponds more particularly to the abovementioned formula (IV). In particular, para-vanillin (called here vanillin) can be produced in vanillate form by oxidation of the corresponding para-mandelic acid.

The alkoxyhydroxybenzaldehyde is obtained by oxidation of the corresponding mandelic compound, preferably in an oxidizing atmosphere, such as $O_2$ or air.

According to one variant, the reaction medium is an alkaline aqueous medium, preferably an inorganic base and more preferably sodium hydroxide or potassium hydroxide, so as to form the corresponding phenate, and to capture the released $CO_2$, in carbonate form.

The reaction may be carried out continuously or batchwise, for example in a medium strongly diluted in water.

The reaction can be catalyzed. A catalyst of this oxidation reaction may be selected from catalysts comprising at least one metal element selected from the group formed by copper, nickel, cobalt, iron, manganese, and any mixture thereof. By way of examples of inorganic or organic copper compounds, mention may in particular be made, as copper compounds, of cuprous and cupric bromide; cuprous iodide; cuprous and cupric chloride; basic cupric carbonate; cuprous and cupric nitrate; cuprous and cupric sulfate; cuprous sulfite; cuprous and cupric oxide; cupric hydroxide; cuprous and cupric acetate; and cupric trifluoromethyl sulfonate. As specific examples of nickel derivatives, mention may be made of nickel(II) halides, such as nickel(II) chloride, bromide or iodide; nickel(II) sulfate; nickel(II) carbonate; the salts of organic acids comprising from 1 to 18 carbon atoms, such as, in particular, acetate or propionate; nickel(II) complexes, such as nickel(II) acetylacetonate, nickel(II) dichlorobis(triphenylphosphine) or nickel(II) dibromobis(bipyridine); and nickel(0) complexes, such as nickel(0) bis(cycloocta-1,5-diene) or nickel(0) bisdiphenylphosphinoethane. As examples of cobalt-based compounds, mention may in particular be made of cobalt(II) and (III) halides, such as cobalt(II) chloride, bromide or iodide or cobalt(III) chloride, bromide or iodide; cobalt(II) and cobalt(III) sulfate; cobalt(II) carbonate, basic cobalt(II) carbonate; cobalt(II) orthophosphate; cobalt(II) nitrate; cobalt(II) and cobalt(III) oxide; cobalt(II) and cobalt(III) hydroxide; the salts of organic acids comprising from 1 to 18 carbon atoms, such as, in particular, cobalt(II) and cobalt(III) acetate or cobalt(II) propionate; cobalt(II) complexes, such as hexaminecobalt(II) or (III) chloride, hexaminecobalt(II) or (III) sulfate, pentaminecobalt(III) chloride or triethylenediaminecobalt(III) chloride. Use may also be made of iron-based catalytic systems, generally in the form of oxides, of hydroxides or of salts, such as iron(II) and iron(III) chloride, bromide, iodide or fluoride; iron(II) and iron(III) sulfate; iron(II) and iron(III) nitrate; or iron(II) and iron(III) oxide. The oxidation reaction can be catalyzed, for example, by a catalytic system comprising two metal elements selected from the group formed by copper, nickel, cobalt, iron, manganese, and any mixture thereof. The present invention covers in particular the reactions described according to patent application WO 08/148760.

Firstly, the mandelate compound reacts with the base (preferably sodium hydroxide) so as to salify the phenate function of the mandelate compound. Then, the oxidation in an oxidizing medium (preferably in air) produces vanillate and $CO_2$ (trapped in carbonate form).

The oxidation of the para-mandelic compound to give para-vanillin is virtually complete, with very good selectivity.

At the end of the oxidation reaction, the precursor of the alkoxyhydroxybenzaldehyde (vanillin and/or ethylvanillin), i.e. with a hydroxyl group in salified (ionic) form, and various impurities, including tars, are obtained.

In a subsequent step, the acidification of the alkoxyhydroxybenzaldehyde (vanillin and/or ethylvanillin) in the reaction medium is carried out using a strong acid, for example sulfuric acid. It is then necessary to recover the noble product, namely the alkoxyhydroxybenzaldehyde (vanillin and/or ethylvanillin), in the presence of tars according to a process which is both friendly to the integrity of the products to be separated while at the same time being economical, and easy to carry out in industrial devices, quite particularly in those which operate continuously. To separate the alkoxyhydroxybenzaldehyde (vanillin and/or ethylvanillin) from the crude reaction mixture, a known method consists in carrying out the extraction thereof using an organic solvent.

Advantageously, the process comprises:
the separation of the alkoxyhydroxybenzaldehyde from the reaction mixture by extraction with an organic solvent; and
the recovery and the recycling of the organic solvent used for the extraction.

Recycling Loop 2

Recycling loop 2 covers the conversion of the alkoxybenzaldehyde hydroxylate (vanillate and/or ethyl vanillate) obtained after the oxidation reaction to give the corresponding alkoxyhydroxybenzaldehyde, and the recovery and the recycling of the solvent used for the extraction of the alkoxyhydroxybenzaldehyde (vanillin and/or ethylvanillin) from the mixture resulting from the oxidation reaction. The invention covers in particular the production of vanillin and/or of ethylvanillin.

The reaction medium resulting from the oxidation is acidified with an acidic medium, preferably containing an inorganic acid, and for example sulfuric acid, or hydrochloric acid, so as to convert the alkoxyhydroxybenzaldehyde salt into alkoxyhydroxybenzaldehyde.

According to one preferred embodiment, the alkoxyhydroxybenzaldehyde contained in the aqueous phase is extracted with an organic solvent which solubilizes the alkoxyhydroxybenzaldehyde contained in the aqueous phase. Use is made of an organic solvent which is inert with respect to the alkoxyhydroxybenzaldehyde. As solvents which can be used, mention may in particular be made of halogenated or nonhalogenated aliphatic, cycloaliphatic or aromatic hydrocarbons; alcohols; ethers; ketones and nitriles. As aliphatic, cycloaliphatic or aromatic hydrocarbons, mention is more particularly made of heptane, cyclohexane, methylcyclohexane, benzene and toluene; as halogenated aliphatic, cycloaliphatic or aromatic hydrocarbons, mention is more particularly made of dichloromethane, trichloromethane, dichloroethane, chlorobenzene and dichlorobenzenes; as alcohols, mention is more particularly made of methanol, ethanol, propanol, isopropanol and butanol; as ethers, mention is more particularly made of diethyl ether, diisopropyl ether and methyl(tert-butyl) ether; as ketones, mention is more particularly made of acetone, methyl ethyl ketone, methyl isobutyl ketone and diisobutyl ketone; and as nitriles, mention is more particularly made of acetonitrile. A mixture of said solvents may be used.

The extraction operation is carried out at a temperature which depends on the nature of the solvent.

This extraction step can be carried out at the same time as the acidification. However, it is preferable for the reaction medium and the organic solvent to be mixed together, and then for the acid to be added.

In order to isolate the alkoxyhydroxybenzaldehyde (vanillin and/or ethylvanillin) from the extraction solvent, a separation step can be carried out by recrystallization, but a distillation of said mixture is preferably carried out, making it possible to obtain, for example at the top of the distillation, the extraction solvent (if it is the most volatile compound of the mixture) and, for example at the bottom of the distillation, a "crude alkoxyhydroxybenzaldehyde" ("crude" vanillin and/or ethylvanillin), namely a mixture comprising essentially the alkoxyhydroxybenzaldehyde, combined with heavy impurities called "tars" and with small amounts of light impurities. Reference is made, for this step in particular, to the process described in patent application WO 2010/007161.

The organic solvent used is advantageously recycled. It can be reintroduced into the process in order to extract the alkoxyhydroxybenzaldehyde from the aqueous phase during the acidification, and/or used to recover the alkoxyhydroxybenzaldehyde from the washing water.

Optionally, the alkoxyhydroxybenzaldehyde can be treated in order to condition it in solid form. Preferably, the alkoxyhydroxybenzaldehyde is purified, preferably by distillation, followed by crystallization (using one or more solvents or by the flaking technique), for example according to the following steps:

dissolution of the alkoxyhydroxybenzaldehyde in a water-alcohol mixture (for example methanol or ethanol);

vacuum crystallization;

batchwise pulling dry;

drying of the alkoxyhydroxybenzaldehyde at a temperature of 25° C. at a temperature below the melting point of the alkoxyhydroxybenzaldehyde, preferably under an inert gas (typically nitrogen).

Several crystallization variants can be envisioned: for example batchwise crystallization, for example by cooling, or continuous crystallization, for example under vacuum.

The resulting product can be optionally ground so as to obtain finer grains.

Other aims, characteristics and advantages of the invention will become clearly apparent to those skilled in the art on reading the explanatory description which refers to examples that are given only by way of illustration and that could in no way limit the scope of the invention.

The examples are an integral part of the present invention and any characteristic appearing to be novel over any prior art on the basis of the description taken as a whole, including the examples, is an integral part of the invention in terms of its function and its generality.

Thus, each example has a general scope.

EXAMPLES

The percentages are given on a weight basis, relative to the total weight of the composition. The temperatures are given in degrees Celsius (° C.).

Example 1

The catechol is reacted continuously in the vapor phase with methanol after vaporization. The resulting mixture comprises catechol, guaiacol, veratrole, 6-methylguaiacol, unreacted methanol, and tars (compound of high molecular weight compared with the other surrounding compounds, for example molecular weight multiplied by 2 or more). Depending on the operating conditions adhered to, the proportions of veratrole, 6-methylguaiacol and tars may be more or less significant in the condensed liquid stream exiting the reaction. Typically, this reaction can be carried out according to patent EP 914 854 B1.

Figure 1:
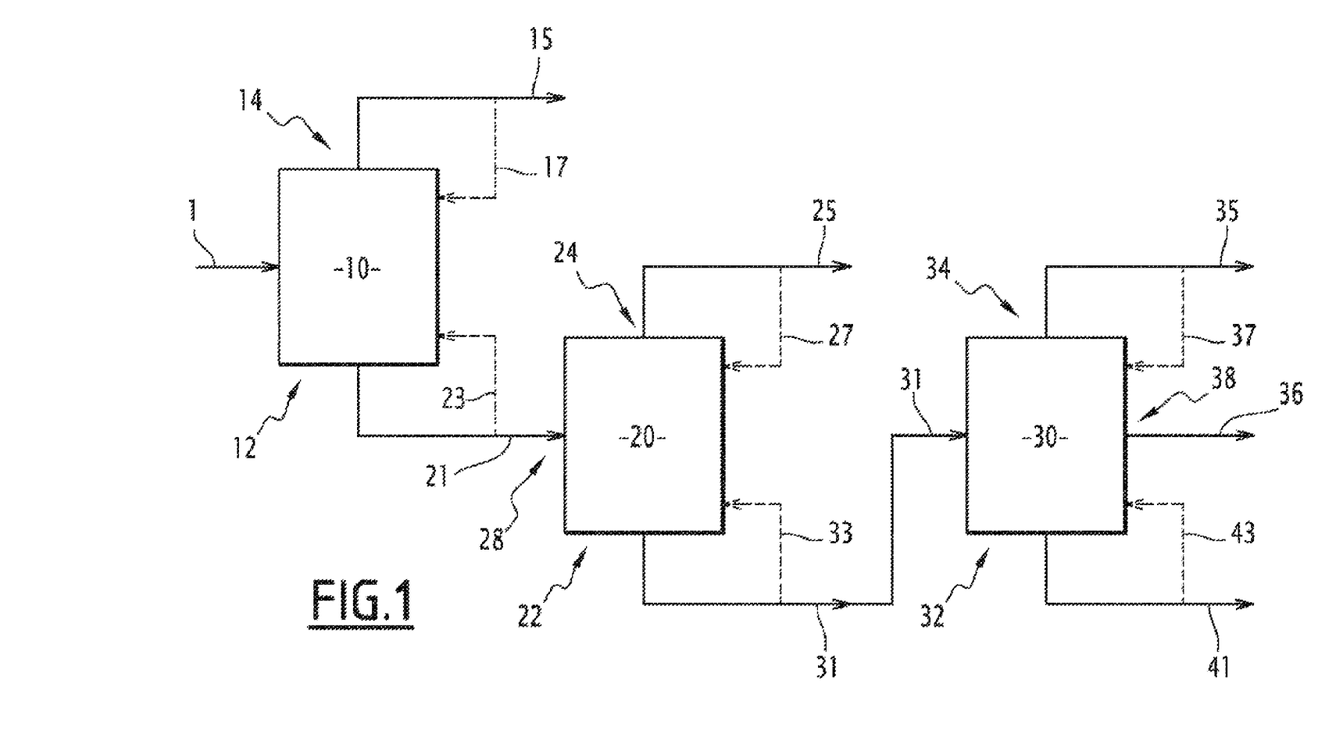
FIGS. 1 and 2 show distillation systems that may be used in embodiments of the disclosure.

The abovementioned resulting mixture was subjected to a continuous distillation using the distillation system shown in FIG. 1 comprising a first distillation column (A) 10, a second distillation column (E) 20 and a third distillation column (F) 30, successively connected in series.

The liquid mixture 1 containing catechol, guaiacol, veratrole, 6-methylguaiacol, unreacted methanol, and tars was fed into the central part of the first distillation column 10 comprising, in its lower part 12, a falling liquid film boiler. The evaporation temperature was 242° C. on average. The first distillation column 10 was operated under conventional conditions so as to separate according to two distinct streams or fractions: the top stream or fraction 15 drawn off from the upper part 14 of column 10, comprising essentially methanol, and the bottom stream or fraction 21 drawn off from the lower part 12 of column 10, comprising essentially the other heavy compounds. The top stream or fraction 15 from the upper part 14 of column 10 was cooled using a condenser so as to at least partially condense the top stream or fraction 15. A part of the top stream or fraction 15 can be introduced, according to a stream or fraction 17, into the upper part 14 of column 10. The output stream 15 from the upper part 14 of column 10 can be purified separately, for example again by distillation using one or more distillation columns. Advantageously, the unreacted methanol is recycled to the reagents of the O-alkylation reaction, after purification. In the lower part 12, a part of the bottom stream or fraction 21 drawn off can be partially reintroduced into the lower part of column 10 according to a stream or fraction 23.

It is thus typically possible to obtain a bottom stream or fraction 21 exiting from the lower part 12 of this first distillation column 10, comprising:
- Catechol (PC): 400 to 600 kg;
- Guaiacol (GA): 400 to 600 kg;
- Veratrole (VER): 10 to 50 kg;
- 6-methylguaiacol (MEGA): 5 to 50 kg;
- Tars: 5 to 100 kg.

The bottom stream 21 conveyed from the lower part 12 of the first distillation column 10 and having a temperature of approximately 115° C. was fed into a central part 28 of a second distillation column 20 and a falling liquid film boiler.

In the second distillation column 20, a top fraction 25 comprising essentially guaiacol and a bottom fraction 31 comprising essentially catechol were generated from the liquid stream 21 that was fed in. The evaporation temperature in the boiler was 155° C. on average, and the temperature in the upper part 24 of column 20 was approximately 110° C. In the lower part 22, a part of the bottom stream or fraction 31 drawn off can be reintroduced into the lower part of the column 20 according to a stream or fraction 33. A part of the top stream 25 drawn off can be introduced, according to a stream or fraction 27, into the upper part 24 of the second column 20.

The distillation in the column 20 is carried out so as to remove from the upper part 24 of the column a maximum amount of guaiacol and, at the bottom, a maximum amount of catechol, of veratrole and of MEGA-6. The bottom liquid stream 31 drawn off from the lower part 22 of the second distillation column 20 was recovered at an average flow rate of approximately 650 kg/hour. The top stream 25 drawn off from the upper part 24 of the second distillation column 20 was recovered at an average flow rate of approximately 570 kg/hour.

The top stream 25 recovered from the upper part 24 of column 20 advantageously comprises:
- Catechol (PC): approximately 0 kg;
- Guaiacol (GA): 400 to 600 kg;
- Veratrole (VER): 0 to 5 kg;
- 6-methylguaiacol (MEGA): 0 to 5 kg;
- Tars: approximately 0 kg.

The bottom stream 31 recovered from the lower part 22 of column 20 advantageously comprises:
- Catechol (PC): 400 to 600 kg;
- Guaiacol (GA): 0 to 50 kg;
- Veratrole (VER): 5 to 50 kg;
- 6-methylguaiacol (MEGA): 0 to 50 kg;
- Tars: 5 to 100 kg.

The bottom stream 31 conveyed from the lower part 22 of the second distillation column 20 was fed into a central part 38 of a third distillation column 30 and a falling liquid film boiler.

The distillation in the third column 30 is carried out so as to draw off, from the upper part 34 of the column, a top stream 35 comprising guaiacol, veratrole, MEGA-6 and catechol, so as to draw off, in the central part 38, a side stream 36 comprising essentially catechol, and so as to draw off, in the lower part 32, a bottom stream 41 comprising a maximum amount of tars.

The top stream 35 containing predominantly catechol had a temperature of approximately 140° C. and was recovered at an average flow rate of approximately 95 kg/hour from the upper part 34 of the third distillation column 30.

In the lower part 32 of column 30, a part of the bottom stream or fraction 41 drawn off can be reintroduced into the lower part 32 according to a stream or fraction 33. In the upper part 34 of column 30, a part of the top stream or fraction 35 drawn off can be reintroduced into the upper part 34 according to a stream or fraction 37.

The bottom stream 41 containing predominantly concentrated catechol had a temperature of approximately 210° C. and was recovered at an average flow rate of approximately 68 kg/hour from the lower part 32 of the third distillation column 30.

The liquid stream 36 containing predominantly concentrated catechol had a temperature of approximately 155° C. and was recovered at an average flow rate of approximately 485 kg/hour from the central part 38 of the third distillation column 30.

The side stream 36 recovered from the central part 38 of column 30 therefore advantageously comprises:
- Catechol (PC): approximately 400 to 600 kg;
- Guaiacol (GA): 0 to 20 kg;
- Veratrole (VER): 0 to 50 kg;
- 6-methylguaiacol (MEGA): 0 to 10 kg;
- Tars: approximately 0 kg.

The top stream 35 recovered from the upper part 34 of column 30 therefore advantageously comprises:
Catechol (PC): 0 to 100 kg;
Guaiacol (GA): 0 to 50 kg;
Veratrole (VER): 0 to 50 kg;
6-methylguaiacol (MEGA): 0 to 50 kg;
Tars: approximately 0 kg.

The bottom stream 41 recovered from the lower part 32 of column 30 therefore advantageously comprises:
Catechol (PC): 0 to 10 kg;
Guaiacol (GA): approximately 0 kg;
Veratrole (VER): approximately 0 kg;
6-Methylguaiacol (MEGA): environ 0 kg;
Tars: 5 to 100 kg.

The distillation columns 20 and 30 advantageously make it possible to separate a top stream 25 at the upper outlet of the second column 20, in the form of optionally condensed vapor, containing predominantly guaiacol, and a side stream 36 at the outlet of the third distillation column 30, in the form of optionally condensed vapor, containing predominantly catechol.

The veratrole and the 6-methylguaiacol impurity can therefore be separated from the stream containing the guaiacol in a manner satisfactory for its subsequent use for the production of aromatic compounds used in particular in the food industry, such as vanillin. The veratrole and the 6-methylguaiacol impurity can also be separated from the stream containing the concentrated catechol in a manner sufficient for envisioning industrial recycling of the catechol. The process according to the present invention enables the recycling of the guaiacol, and also the recycling of the catechol, and has a considerable industrial economic advantage, in particular by virtue of the efficiency of the separation, whether in terms of purity and yield of the products distilled, or of economic profitability.

Example 2

Figure 2:
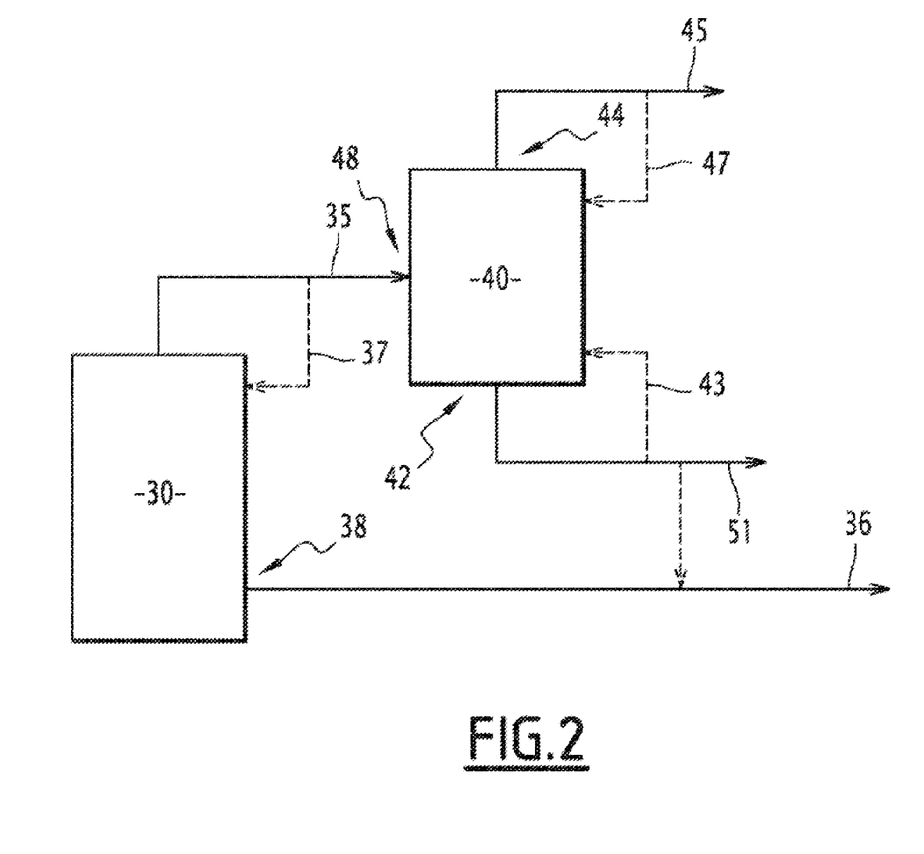

The top stream or fraction 35 drawn off from the third column 30 according to example 1 can be introduced into a fourth distillation column 40 (F2), as illustrated by FIG. 2.

In the fourth distillation column 40, a bottom stream or fraction 51 comprising essentially catechol, and a top stream or fraction 45 containing essentially a mixture of guaiacol, veratrole and MEGA, were generated from the top stream 35 fed in.

The distillation in the fourth column 40 is carried out so as to draw off, from the upper part 44 of the column, a top stream 45 comprising guaiacol, veratrole and predominantly MEGA, and so as to draw off, in the lower part 42, a bottom stream 51 comprising catechol, veratrole and a small proportion of MEGA.

In the lower part 42 of column 40, a part of the bottom stream or fraction 51 drawn off can be reintroduced into the lower part 42 according to a stream or fraction 43. In the upper part 44 of column 40, a part of the top stream or fraction 45 drawn off can be reintroduced into the upper part 44 according to a stream or fraction 47 (not represented).

The top stream 45 had a temperature of approximately 115° C. and was recovered at an average flow rate of approximately 22 kg/hour from the upper part 24 of the second distillation column 20.

The bottom stream 51 had a temperature of approximately 145° C. and was recovered at an average flow rate of approximately 69 kg/hour from the upper part 44 of the fourth distillation column 40.

The bottom stream 51 recovered from the lower part 42 of column 40 therefore advantageously comprises:
Catechol (PC): 40 to 100 kg;
Guaiacol (GA): from 0 to 5 kg;
Veratrole(VER): from 0 to 10 kg;
6-Methylguaiacol (MEGA): from 0 to 5 kg;
Tars: approximately 0 kg.

The stream 51 can advantageously be partially or totally added to the stream 36 drawn off from the side of column 30 before the recycling upstream of the O-alkylation reaction.

The top stream 45 recovered from the upper part 44 of column 40 advantageously comprises:
Catechol (PC): approximately 0 kg;
Guaiacol (GA): from 0 to 20 kg;
Veratrole(VER): from 0 to 10 kg;
6-Methylguaiacol (MEGA): from 5 to 50 kg;
Tars: approximately 0 kg.

Example 3

The stream or fraction (25) comprising guaiacol can be used to prepare the vanillin of high purity from the viewpoint of the MEGA impurity. For the synthesis of vanillin from guaiacol, condensation and oxidation steps can be carried out. These steps are illustrated below in the context of the synthesis of guaiacol obtained in a three-phase (G/L/L) medium, but are directly transposable to the production of vanillin from guaiacol obtained in the vapor phase.

Condensation

The following are continuously charged to a first 5-liter 316 L stainless steel reactor equipped with a jacket, with a mechanical stirrer, with a pH electrode, with a reflux condenser system and with an inert gas inlet:
64.8 kg/h of demineralized water
9.3 kg/h (116 mol/h) of an aqueous solution of sodium hydroxide at 50% by weight
10.1 kg/h (81.5 mol/h) of guaiacol (new and recycled from which all or part of the veratrole has been removed).

This reaction mixture is maintained at a temperature of 35° C. This preparation is then fed into the first reactor of a system of 3 reactors in cascade, with an aqueous solution of glyoxylic acid at 50% by weight (6.04 kg/h, i.e. 40.8 mol/h).

The 3 perfectly stirred reactors are made of 316 L stainless steel and each have a volume of 80 l; they operate at 35° C.

The overall residence time is 2 hours.

At the outlet of the final reactor, a sample of this reaction medium is taken and the compounds present in the mixture are assayed by liquid chromatography.

The results obtained are as follows:
conversion of guaiacol (GA): DC=47%
4-hydroxy-3-methoxymandelic acid (PMA):
YC(PMA)/GA=86%
2-hydroxy-3-methoxymandelic acid:
YC(OMA)/GA=5%
2-hydroxy-3-methoxy-1,5-dimandelic acid:
YC(DMA)/GA=9%.

The reaction medium is sent to recycling loop 1 in order to separate the excess guaiacol from the mandelic compounds.

Oxidation

The 316 L stainless steel oxidation reactor equipped with a self-suction stirrer of cavitation type ("cavitator") or of Rushton type and with a jacket for efficient cooling is continuously fed with:
the mixture of the co-catalysts and of the aqueous solution of mandelic compounds from loop 1, i.e.:
77 kg/h of reaction medium resulting from the condensation reaction, in which the excess guaiacol is removed (then recycled) in recycling loop 1. This mixture contains about 7.2 kg/h of 4-hydroxy-3- methoxymandelic acid, 0.5 kg/h of 2-hydroxy-3-methoxymandelic acid and 0.9 kg/h of 2-hydroxy-3-methoxy-1,5-dimandelic acid;

100 g/h of an aqueous solution of $CoCl_2$ and of $CuSO_4$ in an amount expressed as molar percentage of metal relative to the molar sum of the mandelic acids: 0.04% each;

the appropriate amount of an aqueous solution of sodium hydroxide at 50% by weight corresponding at least to the amount required by the stoichiometry of the oxidation reaction (to be discussed together);

the amount of oxygen at atmospheric pressure sufficient to have a virtually complete conversion of the mandelic acids. The oxidizing agent may be oxygen at atmospheric pressure or pressurized air.

This reaction is carried out at 80° C. At the outlet of the reactor, a sample of this reaction medium is taken and the compounds present in the mixture are assayed by liquid chromatography.

The results obtained are as follows:
conversion of 4-hydroxy-3-methoxymandelic acid: DC>99.5%
Yield of vanillin VA:
YC(VA)/PMA=98%.

The reaction medium is sent to the loop for extraction of the sodium vanillate from the aqueous phase (termed recycling loop 2).

The invention claimed is:

1. A process for producing at least one alkoxyhydroxybenzaldehyde ("AHBA"), said process comprising forming at least one alkoxyphenol ("AP") and at least one alkylalkoxyphenol ("AAP") from at least one hydroxyphenol ("HP") and separating (S) the AP from the AAP, said separating (S) being carried out prior to obtaining AHBA, wherein the AHBA is produced by addition of an aldehyde function to the AP by condensation with glyoxylic acid, followed by oxidation of the resulting compound, and wherein the separating (S) is carried out before the oxidation to give the AHBA compound.

2. The process as claimed in claim 1, wherein the alkoxyhydroxybenzaldehyde (AHBA) is selected from vanillin (VA), ethylvanillin (EVA), and mixtures thereof.

3. The process as claimed in claim 2, wherein the VA, EVA or mixtures thereof is substantially free of 5-methylvanillin ("MEVA") and of 3-ethoxy-5-ethyl-4-hydroxybenzaldehyde ("EEVA"), wherein the AP is selected from guaiacol (GA), guaethol (GE) and mixtures thereof, and wherein the AAP is selected from 6-methylguaiacol ("MEGA"), 6-ethylguaethol ("2-ethoxy-6-ethylphenol" or "EGE"), and mixtures thereof.

4. The process as claimed in claim 1, wherein the separating (S) is carried out before the reaction of AP with glyoxylic acid.

5. The process as claimed in claim 1, wherein the separating (S) is carried out by one or more distillation steps.

6. The process as claimed in claim 1, wherein the process further comprises
introducing a stream or fraction (E1) of a mixture M comprising guaiacol (GA), guaethol (GE), or mixtures thereof, denoted "G", and 6-methylguaiacol (MEGA), 6-ethylguaethol (EGE), or mixtures thereof, denoted "AG", in the presence of pyrocatechol (PC) in a distillation column (E),
recovering G essentially at the top of the distillation column in a stream or fraction (E2), and recovering PC and AG essentially at the bottom of the distillation column in a stream or fraction (E3).

7. The process as claimed in claim 6, wherein the mixture M further comprises a dialkoxybenzaldehyde (DAB), and wherein DAB is recovered essentially at the bottom of the distillation column in the stream or fraction (E3).

8. The process as claimed in claim 6, wherein PC represents from 25% to 75% by weight of the total weight of the stream or fraction (E1).

9. The process as claimed in claim 6, wherein G represents from 25% to 75% by weight of the total weight of the stream or fraction (E1).

10. The process as claimed in claim 6, wherein G represents more than 90% by weight of the total weight of the stream or fraction (E2), and wherein AG represents less than 1% by weight relative to the total weight of the stream or fraction (E2).

11. The process as claimed in claim 6, wherein the stream or fraction (E2) comprises from 90% to 100% of G, from 0 to 1% of AG, and from 0 to 1% of VER, the percentages being expressed by weight relative to the total weight of the stream or fraction (E2).

12. The process as claimed in claim 6, wherein PC represents more than 60% by weight of the total weight of the stream or fraction (E2), and wherein AG represents less than 8% by weight relative to the total weight of the stream or fraction (E3).

13. The process as claimed in claim 6, wherein the stream or fraction (E3) comprises from 60% to 100% of PC, from 0 to 8% of AG, and from 0 to 10% of VER, the percentages being expressed by weight relative to the total weight of the stream or fraction (E3).

14. The process as claimed in claim 6, wherein the process further comprises distilling in a column (F) the stream or fraction (E3) from the bottom of the distillation column (E) by drawing off a stream or fraction (F6) at the side of the column (F) so as to draw off a stream or fraction enriched with PC.

15. A process for separating GA and/or GE from a mixture (M) comprising GA and/or GE and a 6-methylguaiacol ("MEGA") and/or 6-ethylguaethol ("2-ethoxy-6-ethylphenol" or "EGE") impurity, the process comprising introducing the mixture M into a distillation column in the presence of pyrocatechol (PC), recovering a stream or fraction comprising GA and/or GE at the top of the distillation column, and recovering a stream or fraction comprising PC, MEGA and/or EGE at the bottom of the distillation column.

16. A process for synthesizing at least one alkoxyphenol ("AP") in the vapor phase, the process comprising forming at least one AP on the basis of an O-alkylation reaction in the vapor phase, between at least one hydroxyphenol ("HP") and at least one O-alkylating agent, said reaction also forming at least one alkylalkoxyphenol impurity ("AAP"), said reaction thus forming a mixture M comprising AP, AAP and HP, introducing the mixture M into at least one distillation column, recovering a stream or fraction comprising AP at the top of the distillation column, recovering a stream or fraction comprising HP and AAP at the bottom of the distillation column, and optionally recycling the stream or fraction comprising AP downstream of the O-alkylation reaction and/or recycling the stream or fraction comprising HP upstream of the O-alkylation reaction.

17. The process as claimed in claim 16, wherein the AP is selected from guaiacol (GA) and/or guaethol (GE), wherein the HP is pyrocatechol ("PC"), and wherein the AAP is selected from 6-methylguaiacol ("MEGA") and/or 6-ethylguaethol ("2-ethoxy-6-ethylphenol" or "EGE").

* * * * *